United States Patent [19]

Bank

[11] Patent Number: 5,374,761
[45] Date of Patent: Dec. 20, 1994

[54] PROCESS FOR PREPARATION OF ORGANOOXYSILANES

[75] Inventor: Howard M. Bank, Freeland, Mich.

[73] Assignee: Corning Corporation, Midland, Mich.

[21] Appl. No.: 235,736

[22] Filed: Apr. 29, 1994

[51] Int. Cl.$^5$ ............................................... C07F 7/18
[52] U.S. Cl. ................................................. 556/471
[58] Field of Search ...................................... 556/471

[56] References Cited

U.S. PATENT DOCUMENTS

| | | |
|---|---|---|
| 3,008,975 | 11/1961 | Schubert . |
| 3,651,117 | 3/1972 | Bennett . |
| 3,792,071 | 2/1974 | Nitzsche . |
| 3,985,781 | 10/1976 | Kotzsch et al. . |
| 4,039,567 | 8/1977 | Kotzsch et al. . |
| 4,173,576 | 11/1979 | Seiler et al. . |
| 4,298,753 | 11/1981 | Schinabeck et al. . |
| 4,506,087 | 3/1985 | Fischer et al. . |
| 4,924,022 | 5/1990 | Bank et al. . |
| 5,171,476 | 12/1992 | Bloodworth et al. ........... 556/471 X |
| 5,189,194 | 2/1993 | Nguyen ................................ 556/471 |

*Primary Examiner*—Paul F. Shaver
*Attorney, Agent, or Firm*—William F. Boley

[57] ABSTRACT

A process for the organooxylation of chlorosilanes. The process comprises contacting in a film a chlorosilane and an alcohol capable of forming an ester with the silicon of the chlorosilane and thereby forming an equilibrium mixture comprising an organooxysilane and hydrogen chloride. The film is heated at a temperature sufficient to cause vaporization of the hydrogen chloride from the equilibrium mixture thereby increasing the yield of organooxysilane in the equilibrium mixture. In a preferred process, the process is run in a falling-film type reactor or a wiped-film type reactor.

16 Claims, No Drawings

PROCESS FOR PREPARATION OF ORGANOOXYSILANES

BACKGROUND OF INVENTION

The present invention is a process for the organooxylation of chlorosilanes. The process comprises contacting in a film a chlorosilane and an alcohol capable of forming an ester with the silicon of the chlorosilane and thereby forming an equilibrium mixture comprising an organooxysilane and hydrogen chloride. The film is heated at a temperature sufficient to cause vaporization of the hydrogen chloride from the equilibrium mixture thereby increasing the yield of organooxysilane in the equilibrium mixture. In a preferred process, the process is run in a falling-film type reactor or a wiped-film type reactor.

Organooxysilanes prepared by the present process are useful intermediates in the production of other silanes and may be used as coupling agents, silylation agents, and surface treatments. The organooxysilanes are generally safer to handle than the chlorosilanes from which they are formed and the organic substituent of the organooxy group can be tailored to make the organooxysilanes more compatible with organic compounds and materials.

The reaction of an alcohol with a chlorosilane to form an organooxysilane is an equilibrium reaction exemplified by the following equation:

$$\equiv Si-Cl + ROH <-> \equiv SiOR + HCl$$

Therefore, to drive the reaction to favor high yields of the organooxysilane it is desirable to remove the hydrogen chloride as it is formed from the reaction mixture. In addition the hydrogen chloride liberated during the reaction can attack the starting materials and products to produce undesirable by-products which also lowers the yield of the desired products. For example, liberated hydrogen chloride can react with alcohol to produce a hydrocarbon chloride and water. This results in the loss of considerable alcohol. Furthermore, water formed by this side reaction can hydrolyze the chlorosilane producing undesirable polysiloxanes and generating more hydrogen chloride. In addition the hydrogen chloride alone or in combination with the alcohol may react with other functional groups present on the chlorosilanes.

Therefore it is an objective of the present invention to provide a process where hydrogen chloride liberated during the process is rapidly and effectively removed from the reaction mixture. The present inventors have found that this objective can be achieved by running the described equilibrium reaction in a thin-film process. The present process provides an effective means for removing reaction-liberated hydrogen chloride from the process and thereby shifting the chemical equilibrium of the process to favor production of organooxysilanes and also a means for minimizing side reactions and undesired by-products as a result of these side reactions. It is furthermore an objective of the present invention to provide a process with improved mass transfer thereby allowing for more efficient reactor operation than is achieved with reactive-distillation type reactors in which the reaction is typically conducted on a commercial scale.

Various processes have been reported in the art to shift the chemical equilibrium of the reaction of an alcohol with a chlorosilane and to reduce unwanted side reactions.

Schubert, U.S. Pat. No. 3,008,975, issued Nov. 14, 1961, describes a batch process for reacting a chlorosilane with an alcohol. Schubert reports that at reactor pressures below about 200 mm Hg side reactions are reduced and process yield is improved.

Bennett, U.S. Pat. No. 3,651,117, describes a process for reacting a chlorosilane with an alcohol where the chlorosilane, alcohol, and resultant product are kept in the vapor state. Bennett reports this process results in increase process yield and reduced side reactions. Bennett also reports that it may be useful to include in the reaction mixture a base such as ammonia or an amine for the purposes of sequestering hydrogen chloride, to purge the reaction mixture with a gas to remove hydrogen chloride, or to react the reaction mixture with a vicinal alkylene oxide to remove hydrogen chloride.

Nitzsche et al., U.S. Pat. No. 3,792,071, issued Feb. 12, 1974, describe the use of a fractional distillation column for the reaction of an alcohol with a chlorosilane. The chlorosilane is introduced at the head of the column and the alcohol is introduced in the gaseous form from below or at a point in the lowest one-third of the length of the column. For at least two-thirds of the zone between the inlet of the alcohol and the inlet of the silane into the column the column is maintained over its entire internal cross-section at a temperature at least 0.5° C. above the boiling point of the particular alcohol used.

Kotzsch et al., U.S. Pat. No. 3,985,781, issued Oct. 12, 1976, report a two-step batch process where in the first step a primary alcohol is contacted with a trichlorosilane sufficient to effect only partial esterification of the trichlorosilane. The hydrogen chloride is then removed from the reactor by heating and then additional alcohol is added to the reactor to complete the esterification process.

Kotzsch et al., U.S. Pat. No. 4,039,567, issued Aug. 2, 1977, describe a process for reacting a chlorosilane with an alcohol in a distillation column. The process comprises feeding a liquid alcohol and a liquid chlorosilane into a distillative reaction zone having a head portion and a sump portion. The head portion is maintained at a temperature sufficient for the esterification reaction to occur and gaseous hydrogen chloride formed by the reaction is continuously distilled off.

Seiler et al. U.S. Pat. No. 4,173,576, issued Nov. 6, 1979, describe an improved process for the esterification of chlorosilanes with alcohols. The esterification process is carried out in the presence of a chlorohydrocarbon and in the absence of an acid binding agent. Seiler et al. state that it has been proposed to purge out the hydrogen chloride forming as a result of the process by passing an inert gas over the surface or through the reaction mixture with the aid, in some cases of a falling film evaporator. Seiler et al. conclude that this in an impractical approach due to the quantity of exhaust gas created, loss of product, and need for large capacity cooling apparatuses.

Schinabeck et al., U.S. Pat. No. 4,298,753, issued Nov. 3, 1981, describe a continuous two-stage process for preparing alkoxysilanes. The process comprises introducing in a liquid phase a chlorosilane and a hydroxyl-containing aliphatic compound in parallel flow into a first reactor; then removing the liquid reaction mixture from the first reactor and introducing it at the head of a column used as the second reactor, which is maintained at an elevated temperature, and adding a hydroxyl-containing aliphatic compound as a gas at the lower end of the column. An alkoxysilane product is recovered from the bottom of the column.

Fischer et al., U.S. Pat. No. 4,506,087, issued Mar. 19, 1985, teach a continuous process for preparation of alkoxysilanes with hydrogen chloride contents of less than 20 ppm. In the described method, the esterification is performed in a reaction vessel and the raw esterification product is continuously removed and delivered to the top of a column. In this column, the reactant alcohol is vaporized and condensed at the top. The raw product drips from the top of the column to the bottom where it is collected.

Bank et al., U.S. Pat. No. 4,924,022, issued May 8, 1990, teach a continuous system for the manufacture of organoalkoxysilanes. The reactor consists of a fractionating column that allows for completion of the reaction and separation of the hydrogen chloride formed as a by-product.

The cited art does not recognize that the esterification reaction of alcohol with a chlorosilane can be conducted as a thin-film process thereby effecting efficient vaporization and removal of hydrogen chloride from the process. The present process can increase yield of organooxysilane product and reduced undesired side reactions. The present process can also provided for comparable yields in simpler and smaller reactors, when compared to typical reactive distillation processes in current commercial use.

SUMMARY OF INVENTION

The present invention is a process for the organooxylation of chlorosilanes. The process comprises contacting in a film a chlorosilane and an alcohol capable of forming an ester with the silicon of the chlorosilane and thereby forming an equilibrium mixture comprising an organooxysilane and hydrogen chloride. The film is heated at a temperature sufficient to cause vaporization of the hydrogen chloride from the equilibrium mixture thereby increasing the yield of organooxysilane in the equilibrium mixture. In a preferred process, the process is run in a falling-film type reactor or a wiped-film type reactor.

DESCRIPTION OF INVENTION

The present invention is a process for organooxylation of chlorosilanes. The process comprises:

(A) contacting in a film a chlorosilane described by formula $$R_nSiCl_{4-n} \qquad (1)$$

with an alcohol capable of effecting esterification with the silicon atom of the chlorosilane thereby forming an organooxysilane and hydrogen chloride, (B) vaporizing the hydrogen chloride from the film to facilitate formation of the organooxysilane, and (C) recovering the organooxysilane; where each R is independently selected from a group consisting of hydrogen, monovalent hydrocarbon radicals comprising one to about 20 carbon atoms, and halogen-substituted monovalent hydrocarbon radicals comprising one to about 20 carbon atoms, and n=0, 1, 2, or 3.

Chlorosilanes useful in the present process are described by formula (1). The esterification reaction of the present process requires that the chlorosilane have at least one chlorine substituent on the silicon atom and as many as four chlorine substituents may be present on the silicon atom.

The chlorosilane can have zero, one, two, or three substituents R, where each R is independently selected from a group consisting of hydrogen, unsubstituted monovalent hydrocarbon radicals comprising one to about 20 carbon atoms and halogen-substituted monovalent hydrocarbon radicals comprising one to about 20 carbon atoms. In addition to hydrogen, R may be for example alkyls such as methyl, ethyl, propyl, butyl, isobutyl, sec-butyl, octyl, octyldecyl, and 2-ethylhexyl; alkenyls such as vinyl and allyl; hexadienyls; cycloalkyls such as cyclopentyl, cyclohexyl, and cycloheptyl; aromatic hydrocarbon radicals such as phenyl and naphthyl; aralkyls such as benzyl, 2-phenylethyl, and 2-phenylpropyl; alkaryls such as tolyl and dimethylphenyl; and halogen-substituted hydrocarbon radicals such as chloromethyl, 3-chloropropyl, and 3,3,3-trifluoropropyl.

Chlorosilanes useful in the present process can include for example: chlorosilane ($H_3SiCl$), trichlorosilane, tetrachlorosilane, methyldichlorosilane, dimethyldichlorosilane, trimethylchlorosilane, ethyldichlorosilane, vinyltrichlorosilane, methylvinyldichlorosilane, phenyldichlorosilane, phenyltrichlorosilane, diphenyldichlorosilane, methylhexadienyldichlorosilane, (chloropropyl)trichlorosilane, bis-(3,3,3-trifluoropropyl)dichlorosilane, and tris-(3,3,3-trifluoropropyl)chlorosilane.

The chlorosilane is contacted with an alcohol capable of effecting esterification with the silicon atom of the chlorosilane to form an organooxysilane and hydrogen chloride. In the present process the term "alcohol" refers to those compounds containing only carbon, hydrogen, and oxygen, only one hydroxyl group bonded only to a non-carboxyl containing carbon atom, and any other oxygen in the alcohol is an ether group or part of an oxide or ester structure. Any alcohol which under the conditions of the present process is capable of effecting esterification with the silicon atom of the chlorosilane may be used. The only limitation imposed in the selection of such an alcohol is the practical considerations of the boiling point of the alcohol.

Suitable alcohols for the present process may include -methanol, ethanol, n-propanol, isopropanol, n-butanol, isobutanol, tertiary butyl alcohol, n-pentanol, isopentanol, n-hexanol, 2-ethyl-n-hexanol, allyl alcohol, cyclohexanol, phenol, benzyl alcohol, 2-methoxyethanol, 2-ethoxyethanol, and 2-butoxyethanol.

Preferred is when the alcohol is a primary alkanol comprising about one to 12 carbon atoms. Most preferred is when the alcohol is selected from a group consisting of methanol and ethanol.

The molar ratio of alcohol to chlorosilane used in the present process will depend upon the number of silicon-bonded chlorine atoms and the number of such chlorine atoms on each silicon that are desired to be replaced with an organooxy group.

In general when it is desired to replace all of the chlorine atoms bonded to silicon, the molar ratio of alcohol to chlorosilane can be varied within a range of about 60 to 140 percent of stoichiometric equivalence. However, it is preferred that the molar ratio of alcohol to chlorosilane be within a range of about 95 to 110 percent of stoichiometric equivalence. Most preferred is when the molar ratio of alcohol to chlorosilane is within a range of about 100 to 105 percent of stoichiometric equivalence. Stoichiometric equivalence herein is defined as one mole of alcohol per mole of silicon-bonded chlorine added to the process as chlorosilane.

The alcohol and chlorosilane are contacted in a film. In the present process, either the alcohol or the chlorosilane or both must be in the liquid phase. However, those skilled in the art will appreciate that to form the film only one of the reactants need be in the liquid phase and the other can be contacted with the film as a vapor. Therefore, the alcohol, the chlorosilane, or both may be preheated prior to contact as long as the above condition of at least one of the reactants being in a liquid phase is met. In a preferred process, a film of the chlorosilane is formed and the alcohol is contacted with the film as a vapor.

The method of forming the film is not critical to the present process and can be any of those known in the art. The benefit of the present process is realized by the efficient mass transfer characteristics of the film allowing for a rapid vaporization and removal of hydrogen chloride from the film. The vaporization and removal of hydrogen chloride from the film results in a shift of the chemical equilibrium of the reaction to favor production of organooxysilanes and minimizes undesired side reactions as previously described.

The film can be formed, for example, in a falling film evaporator-type apparatus or in a wiped film evaporator-type apparatus. Examples of such apparatus are described, for example, in Kirk-Othmer, *Encyclopedia of Chemical Technology*, Fourth Edition, Vol. 9, p. 965–968, 1984; and in Mehra, "Selecting Evaporators," *Chemical Engineering*, Feb. 3, 1986, p. 56–72. The film forming apparatus employed as a reactor in the present process may be connected to a reboiler. The reactor may be used as a multiple-pass reactor, where materials exiting the reactor are recycled to the reactor to effect further reaction of the materials. Materials exiting the reactor may be fed to one or more similar reactors connected in series to effect further reaction. Product from the reactor may act as a feed to other processes for further reacting and purifying the product, for example, distillation or reactive distillation processes.

Film thickness and flow rates will depend upon such factors as minimum wetting rate for the surface on which the film is formed and the flooding point for the film. Standard methods for determining these parameters are described, for example, in Perry et al., *Perry's Chemical Engineers' Handbook*, 6th Ed., McGraw-Hill, NY, p. 5–59, (1994); and in York et al., *Chemical Engineering Progress*, Oct., 1992, p. 93–98. The term "film" is meant to include the coating or spreading of a bulk liquid onto a surface so as to increase the surface area of the bulk liquid and thereby increase mass transfer of components from the liquid to a vapor phase.

Hydrogen chloride formed as a result of the contact of the alcohol with the chlorosilane is vaporized from the film. Vaporization of the hydrogen chloride is effect by heating the film, by reducing pressure over the film, or by a combination of both. It is preferred that vaporization of the hydrogen chloride from the film be effected by heating the film. The film can be heated by standard methods, for example, passing a heated media such as a gas, water, or silicone oil through a jacket contacting a wall supporting the film. The film can be heated by heating one of the feed materials to the process above its vaporization point and contacting the vapor with the film. For example, the alcohol can be heated above its vaporization point and fed to a reactor counter current to the flow of a film of the liquid chlorosilane. Generally, it is preferred that the temperature of the film be as great as possible without effecting significant vaporization of the film. Within these general guidelines optimal temperatures for running the present process will depend upon the specific alcohol, chlorosilane, and optional solvent used in the process.

An inert solvent may be used in the present process. The solvent may serve, for example, as a refluxing aid, diluent, carrier, or heating means in the present process. Generally, any inert solvent which does not enter into the reaction nor adversely affect the rate of reaction can be used. Preferred are those inert solvents which are liquid under normal conditions and have a boiling point below about 150° C. Examples of such solvents include hydrocarbon solvents such as toluene, xylene, hexane, nonane, pentane, and butane and chlorinated hydrocarbons exemplified by carbon tetrachloride, chloroform, methylene chloride, dichloroethane, dichloroethylene, 1,1,1-trichloroethane, trichloroethylene, perchloroethylene, and tetrachloroethane.

The hydrogen chloride vaporized from the present process is removed from the reactor by standard methods, for example venting, and can be collected and used as a feed to other processes.

Organooxysilanes are recovered from the present process. The organooxysilanes which can be recovered from the present process are described by reference to formula (1), where one or more of the chlorine substituents of the silicon atom of the chlorosilane is replaced by an organooxy radical. Preferred organooxysilanes prepared by the present process are those where in formula (1) all of the chlorine atoms bonded to the silicon atom are replaced by organooxy radicals.

The organooxysilane can be for example methoxysilane, ethoxysilane, butoxysilane, dimethyldimethoxysilane, dimethylmethoxychlorosilane, trimethoxysilane, tetramethoxysilane, tert-butyltrimethoxysilane, isobutyltrimethoxysilane, isobutylmethoxysilane, octadecyltrimethoxysilane, cyclohexylmethyldimethoxysilane, triethoxysilane, methylvinyldimethoxysilane, phenyldimethoxysilane, diphenyldimethoxysilane, phenylmethoxychlorosilane, triphenylmethoxysilane, 2-phenylpropylmethyldimethoxysilane, methylhexadienyldimethoxysilane, (chloropropyl)trimethoxysilane, (3,3,3-trifluoropropyl)trimethoxysilane, bis-(3,3,3-trifluoropropyl)dimethoxysilane, and tris-(3,3,3-trifluoropropyl)methoxysilane.

Recovery of the organooxysilane from the present process may consist of simply retaining an organooxysilane containing liquid mixture resulting from the contact of the alcohol with the chlorosilane in a film. Recovery of the organooxysilane can consist of using the organooxysilane containing liquid mixture as a feed, for example, to another similar reactor or a reactive distillation column to effect further reaction of the mixture. Recovery of the organooxysilane can consist of standard separation processes, such as distillation, to further isolate the organooxysilane.

The following examples are provided to illustrate the present invention. These examples are not intended to limited the scope of the claims herein.

EXAMPLE 1

The methoxylation of trichlorosilane in a falling-film type reactor was evaluated. The falling-film type reactor comprised a 7.6 cm inside diameter by 25 cm length glass tube. Positioned 5 cm from the top of the reactor were three teflon wipe blades 15 cm in length which were held against the reactor wall by centrifugal action. The outside of the reactor had a heating jacket positioned 10 cm below the top of the reactor and ending 4 cm from the bottom. Thermocouples for temperature determination were positioned in the void volume of the reactor above and below the level of the heating jacket. The top of the reactor was connected to a dry ice condenser. The bottom of the reactor was connected to a reboiler. Methanol was vaporized and fed to the reactor through a port located above the reboiler and below the blades of the reactor. During the run product was continuously collected from the reboiler at a rate equal to the filling rate so as to maintain a constant volume in the reboiler.

To conduct the run, the reboiler was charged with 150.0 g of xylene which was heated to 75° C. A mixture of 381.1 g of trichlorosilane and 254.0 g of xylene was fed to the top of the reactor at a rate of 5.07 mL/min. and vaporized methanol was fed to the reactor through the bottom port at about 99 percent stoichiometric equivalence. No heat was provided to the reactor by means of the heating jacket during this run. During the run the upper void temperature of the reactor was about 43° C. and the lower void temperature about 60° C. At the end of two hours a sample was taken from the reboiler and analyzed by gas liquid chromatography using a thermal conductivity detector (GLC-TC). The area percent under the GLC-TC trace was determined for each of the following components: 0% chlorodimethoxysilane, 40.8% trimethoxysilane, 0.4% tetramethoxysilane, and 58.1% xylene. The chlorine content of a sample taken from the reboiler was determined by KOH titration using BCP as an indicator. The sample was determined to have 0.06 weight percent chlorine.

EXAMPLE 2

The methoxylation of methylvinyldichlorosilane in a wiped-film type reactor was evaluated. The reactor was similar to that described in Example 1. The reboiler was charged with 150.0 g of toluene which was initially heated to 100° C. and allowed to dropped to 70° C. during the course of the run. Methylvinyldichlorosilane was fed to the top of the reactor at a rate of 3.23 mL/min. and vaporized methanol was fed to the reactor through the bottom port at about 120 percent stoichiometric equivalence. No heat was provided to the reactor by means of the heating jacket during this run. During the run the upper void temperature of the reactor was about 57° C. and the lower void temperature about 65° C. At the end of 2.3 hours the content of the reboiler was analyzed by GLC using a flame ionization detector (GLC-FID) and KOH titration as described in Example 1. The analysis showed 7.4% methylvinylchloromethoxysilane, 77.3% methylvinyldimethoxysilane, 6.3% toluene, 2.0% of the disiloxane MeVi(MeO)Si)₂(where Me=methyl and Vi=vinyl), and 2.6 to 3.0 weight percent chlorine.

EXAMPLE 3

The methoxylation of methyldichlorosilane in a wiped-film type reactor was evaluated. The reactor was similar to that described in Example 1. The reboiler was charged with 150 g of toluene which was heated to a temperature of 70° C. A mixture comprising 460.1 g of methyldichlorosilane and 307.4 g of toluene was fed to the top of the reactor at a rate of 0.024 moles/min. of the methyldichlorosilane and vaporized methanol was fed to the reactor through the bottom port at about 100 to 103 percent of stoichiometric equivalence. No heat was provided to the reactor by means of the heating jacket during this run. At the end of 3.6 hours the content of the reboiler was analyzed by GLC-TC and KOH titration as described in Example 1. The analysis showed 1.2% methanol, 1.9% methylmethoxychlorosilane, 20.3% methyldimethoxysilane, 4.9% methyltrimethoxysilane, 71.5% toluene, and 2.3 weight percent chlorine.

I claim:

1. A process for preparing organooxysilanes, the process comprising:
   (A) contacting in a film a chlorosilane described by formula

   $$R_nSiCl_{4-n}$$

with an alcohol capable of effecting esterification with the silicon atom of the chlorosilane thereby forming an organooxysilane and hydrogen chloride,
   (B) vaporizing the hydrogen chloride from the film to facilitate formation of the organooxysilane, and
   (C) recovering the organooxysilane; where each R is independently selected from a group consisting of hydrogen, monovalent hydrocarbon radicals comprising one to about 20 carbon atoms, and halogen-substituted monovalent hydrocarbon radicals comprising one to about 20 carbon atoms, and n=0, 1, 2, or 3.

2. A process according to claim 1, where the alcohol is a primary alkanol comprising about one to 12 carbon atoms.

3. A process according to claim 1, where the alcohol is selected from a group consisting of methanol and ethanol.

4. A process according to claim 1, where the molar ratio of the alcohol to the chlorosilane is within a range of about 60 to 140 percent of stoichiometric equivalence.

5. A process according to claim 1, where the molar ratio of the alcohol to the chlorosilane is within a range of about 95 to 110 percent of stoichiometric equivalence.

6. A process according to claim 1, where the molar ratio of the alcohol to the chlorosilane is within a range of about 100 to 105 percent of stoichiometric equivalence.

7. A process according to claim 1, where a film of the chlorosilane is formed and the alcohol is vaporized and contacted with the film.

8. A process according to claim 1, where the film is formed in a falling film evaporator-type apparatus.

9. A process according to claim 1, where the film is formed in a wiped film evaporator-type apparatus.

10. A process according to claim 1, where the vaporizing of the hydrogen chloride from the film is facilitated by heating the film.

11. A process according to claim 1, further comprising the use of an inert solvent.

12. A process according to claim 1, where all the chlorine atoms bonded to the silicon atom of the chlorosilane are replaced by organooxy radicals.

13. A process according to claim 1, where the recovered organooxysilane is selected from a group consisting of trimethoxysilane, methylvinyldimethoxysilane, and methyldimethoxysilane.

14. A process according to claim 1, where the alcohol is a primary alkanol comprising about one to 12 carbon atoms, the molar ratio of the alcohol to the chlorosilane is within a range of about 100 to 105 percent of stoichiometric equivalence, a film of the chlorosilane is formed and the alcohol is vaporized and contacted with the film, and vaporizing of the hydrogen chloride from the film is facilitated by heating the film.

15. A process according to claim 14, where the alcohol is selected from a group consisting of methanol and ethanol.

16. A process according to claim 15, where the recovered organooxysilane is selected from a group consisting of trimethoxysilane, methylvinyldimethoxysilane, and methyldimethoxysilane.

* * * * *